United States Patent
Maalawy

(10) Patent No.: US 10,137,079 B2
(45) Date of Patent: Nov. 27, 2018

(54) TRANSDERMAL COMPOSITION FOR TREATING PAIN

(71) Applicant: Cura Health Inc., Mississauga (CA)

(72) Inventor: Moheb Maalawy, Mississauga (CA)

(73) Assignee: CURA HEALTH INC., Mississauga, Ontario (CA)

( * ) Notice: Subject to any disclaimer, the term of this patent is extended or adjusted under 35 U.S.C. 154(b) by 154 days.

(21) Appl. No.: 15/120,298

(22) PCT Filed: Feb. 20, 2014

(86) PCT No.: PCT/CA2014/050117
§ 371 (c)(1),
(2) Date: Aug. 19, 2016

(87) PCT Pub. No.: WO2015/123750
PCT Pub. Date: Aug. 27, 2015

(65) Prior Publication Data
US 2017/0049694 A1    Feb. 23, 2017

(51) Int. Cl.
| | |
|---|---|
| A61K 9/00 | (2006.01) |
| A61K 47/10 | (2017.01) |
| A61K 47/24 | (2006.01) |
| A61K 31/165 | (2006.01) |
| A61K 45/06 | (2006.01) |
| A61K 31/045 | (2006.01) |
| A61K 31/125 | (2006.01) |
| A61K 33/06 | (2006.01) |
| A61K 9/70 | (2006.01) |
| A61K 47/02 | (2006.01) |
| A61K 9/127 | (2006.01) |

(52) U.S. Cl.
CPC .......... *A61K 9/0014* (2013.01); *A61K 9/1271* (2013.01); *A61K 9/7015* (2013.01); *A61K 31/045* (2013.01); *A61K 31/125* (2013.01); *A61K 31/165* (2013.01); *A61K 33/06* (2013.01); *A61K 45/06* (2013.01); *A61K 47/02* (2013.01); *A61K 47/10* (2013.01); *A61K 47/24* (2013.01)

(58) Field of Classification Search
None
See application file for complete search history.

(56) References Cited

U.S. PATENT DOCUMENTS

| | | | | |
|---|---|---|---|---|
| 5,716,638 | A | * | 2/1998 | Touitou ............... A61K 8/14 264/4.1 |
| 5,807,746 | A | | 9/1998 | Lin |
| 5,922,332 | A | * | 7/1999 | Fossel ............... A61K 8/0208 424/401 |
| 6,841,535 | B2 | | 1/2005 | Divita |
| 2010/0197598 | A1 | | 8/2010 | Woong |

OTHER PUBLICATIONS

International Search Report dated Sep. 1, 2014, for International Application No. PCT/CA2013/000614 (WO2014005219).
Aute et al. International Journal of Research and Development in Pharmacy and Life Sciences, vol. 2 (1), pp. 218-224, 2012.
Pathan and Setty, Trop J Pharm Res, vol. 8 (2) p. 173, 2009.
Touitou et al. (Journal of Controlled Release, vol. 65, pp. 403-418, 2000.
Akiladevi, D. et al. International Journal of Current Pharmaceutical Research, vol. 2(4), pp. 1-4, 2010.
Zhang, J-P. et al., Archives of Pharmacol Research, vol. 35(1), pp. 109-117, 2012.
Jump, T., Sherwood, L. Human Physiology West Publ. Co. Minneapolis USA 1993; Smith, J.S. et al. Journal of General Physiology, vol. 88, pp. 573-588, 1986.
Smith, J.S. et al. Journal of General Physiology vol. 88, pp. 573-588, 1986.
Laver, D.R. et al. The Journal of Membrane Biology vol. 156, pp. 213-229, 1997.
Eisenkraft et al. Military Medicine vol. 174(1), pp. 47-52, 2009.
Xu et al. The Journal of Neuroscience 25(39):8924-8937, 2005.
Paolino, D. et al. Journal of Controlled Release, vol. 106, pp. 99-110, 2005.
Manconi, et al., Colloids and Surfaces A: Physicochem. Eng. Aspects vol. 342 pp. 53-58 , 2009.
Ahem, G. P. et al. The Journal of Neuroscience, vol. 25(21), pp. 5109-5116, 2005.

* cited by examiner

*Primary Examiner* — Nannette Holloman
(74) *Attorney, Agent, or Firm* — Snell & Wilmer LLP

(57) ABSTRACT

Described is a transdermal ethosome composition for the treatment of pain. The transdermal ethosome composition comprises: an alcohol; a phospholipid; water; and a magnesium salt, a TRPV1 receptor agonist, or both a magnesium salt and a TRPV1 receptor agonist. The present compositions can be used to treat pain that is muscular, nociceptive or neuropathic in origin.

24 Claims, No Drawings

TRANSDERMAL COMPOSITION FOR TREATING PAIN

CROSS-REFERENCE TO RELATED APPLICATIONS

This application is a U.S. National Phase filing under U.S.C. § 371 of PCT Patent Application No. PCT/CA2014/050117, filed Feb. 20, 2014, and entitled "Transdermal Composition for Treating Pain," which is incorporated herein by reference in its entirety.

FIELD OF THE INVENTION

The present invention pertains to a topical composition for use in the treatment of pain. More particularly, the present invention pertains to a transdermal ethosome composition comprising a compound for treating pain.

BACKGROUND

The skin is a multi-layered structure made up of stratum corneum, under which lies the epidermis and dermis. The dermis contains blood vessels as well as nerves and nerve endings which are sensitive to touch and pain. The barrier structure of the stratum corneum makes the stratum corneum about 1000 times less permeable than other biological membranes and presents a major challenge for transdermal delivery of active pharmaceutical ingredients to the dermis (Aute et al. *International Journal of Research and Development in Pharmacy and Life Sciences*, Vol. 2 (1), pp. 218-224, 2012).

Permeation of a drug through skin can be enhanced by both chemical penetration enhancement and physical methods (Pathan and Setty, *Trop J Pharm Res*, Vol. 8 (2) p. 173, 2009). One method of enhancing skin penetration of active pharmaceutical ingredients (APIs) is by encapsulating the API in an ethosome. Ethosomes comprise mainly alcohol, water and phospholipid, and were previously described by Touitou et al. (*Journal of Controlled Release*, Vol. 65, pp. 403-418, 2000, U.S. Pat. No. 5,716,638). Touitou et al. demonstrates that ethosomal systems are more efficient at delivering a fluorescent probe to the skin in terms of quantity and depth than either liposomes or hydroalcoholic solutions.

Ethosomes have also been found to have a high entrapment capacity for molecules of various lipophilicities, and to be capable of encapsulating hydrophilic drugs, cationic drugs, proteins and peptides. Some examples of drug molecules that have been formulated with ethosomes for transdermal delivery are cannabinoids, testosterone, minoxidil, propranolol, trihexaphenidyl, zidovudine, bacitracin, erythromycin, acyclovir, methotrexate, cyclosporine, insulin and salbutamol (Akiladevi, D. et al. *International Journal of Current Pharmaceutical Research*, Vol. 2, Iss. 4, 2010; Aute et al. *International Journal of Research and Development in Pharmacy and Life Sciences*, Vol. 2, No. 1, pp 218-224, December-January, 2012-13).

It has been suggested that the relatively high concentration of ethanol (20-50%) in vesicular form in ethosomes is the main reason for their good skin permeation ability, and that ethanol acts to disturb the skin lipid bilayer organization. The presence of ethanol in the ethosome also yields a softer and malleable vesicle structure, which gives more freedom, elasticity and stability to its membrane. The ethosomal transdermal drug delivery system has been reported to improve skin delivery of various drugs in vitro and in vivo (Zhang, J.-P. et al., *Archives of Pharmacal Research*, Vol. 35(1), pp. 109-117, 2012). Some benefits of using ethosomes in particular as a transdermal drug delivery carrier include: deep penetration of the medication; penetration through skin to reach muscles and deep nerves where the pain can be successfully treated; safe ingredients; easy to apply; dries quickly with no mess; starts to work in minutes; and long lasting effects.

Transdermal formulations can be used to treat pain and inflammation that is of soft tissue in origin. This can be due to injury to tendons, ligaments, muscles and joints, such as sprains and strains, as well as due to neurological issues caused by soft tissue rheumatism and osteoarthritis in peripheral joints such as those in the knee or hand. Muscle pain is often due to focal muscular contraction or contraction at a trigger point.

Magnesium cation ($Mg^{2+}$) has been shown to have inhibitory action on the release of $Ca^{2+}$ from the sarcoplasmic reticulum in skeletal muscles, and increased amounts of magnesium near muscles has been shown to result in relaxation of the muscle (Jump, T., Sherwood, L. *Human Physiology* West Publ Co. Minneapolis USA 1993; Smith, J. S. et al. *Journal of General Physiology* Vol. 88, pp. 573-588, 1986). The effect of local action of magnesium on skeletal muscles is as a topical muscle relaxant, by blocking calcium from entering the muscle to cause contraction (Laver, D. R. et al. *The Journal of Membrane Biology* Vol. 156, pp. 213-229, 1997). Magnesium is also essential for the formation of ATP that is needed to cause the relaxation of the muscle and the exocytosis of calcium from muscle fibre cells. Magnesium also acts on the glutamate receptor which has been implicated in numerous neurological disorders. Increasing local magnesium concentration near neurons has also been found to block the transmission of action potential to the muscles by calcium-gated ion channel, and also to block N-methyl-D-aspartate (NMDA) receptors, which are a kind of glutamate receptor. Magnesium has been found to be a natural block for the NMDA receptor. In blood vessels, locally high levels of magnesium have also be shown to act as calcium channel blockers to causes blood vessel dilatation, which can lead to improved local circulation. Better circulation means more blood to an area of pain or injury, which can provide additional physiological support and energy for healing. Magnesium has also been found to have inhibitory activity on Ryanodine receptors, which are receptors involved in muscle contraction. However, it has been found that direct application of magnesium cation on the skin, even in high concentrations, does not result in any significant skin penetration (Eisenkraft et al. *Military Medicine* Vol. 174(1), pp. 47-52, 2009).

The vanilloid receptor (TRPV1) is one of six sub-members that belong to the transient receptor potential channel (TRP) superfamily. TRPV1 is a non-selective cation channel permeable for calcium found on nociceptors that provides the sensation of scalding heat and pain. Activation of TRPV1 sets off an influx of calcium and sodium ions which in turn initiates a cascade of events that result in membrane depolarization, neuronal firing and transduction of neural impulses. TRPV1 exhibits two types of desensitization: acute desensitization, which is the diminished response during a constant agonist application, and tachyphylaxis, which is the reduction of the response to multiple stimuli (Xu et al. *The Journal of Neuroscience* 25(39):8924-8937, 2005).

Capsaicin is a naturally occurring vanilloid which acts as an agonist to TRPV1. Capsaicin has demonstrated positive effects in the treatment of nociceptive pain, such as arthritis, and neuropathic pain, such as diabetic foot. Resiniferatoxin (RTX) and allyl isothiocyanate are other naturally occurring compounds that exhibit TRPV1 agonistic activity. However, delivery of capsaicin and other TRPV1 agonists, or TRPV1 antagonists to the TRPV1 receptor has proven challenging, especially because even small doses of these compounds can cause perceptible and sometimes intolerable burning sensation to the skin.

There remains a need for a transdermal composition for the treatment of pain.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a transdermal ethosome composition for the treatment of pain. In some embodiments, the present compositions can be used to treat pain caused by muscle tightness, rigidity or soreness. In other embodiments, the present compositions can be used to treat neuropathic or nociceptive pain. In other embodiments, the present compositions can be used to increase subdermal concentration of magnesium.

In one aspect there is provided a transdermal ethosome composition comprising: an alcohol; a phospholipid; a glycol; water; and a magnesium salt.

In one embodiment, the alcohol is present in an amount of between about 20-50% by weight of the composition, the phospholipid is present in an amount of between about 1-3% by weight of the composition, the glycol is present in an amount of between about 5-20% by weight of the composition, and the water is present in an amount of between about 20-70% by weight of the composition.

In another embodiment, the magnesium salt is present in the ethosome composition in an amount of between about 5.0-15.0% by weight of the composition.

In another embodiment, the phospholipid comprises lecithin, a phospholipid derived from lecithin, or phosphatidyl choline.

In another embodiment, the alcohol is ethanol, isopropanol, or a combination thereof.

In another embodiment, the composition further comprises at least one additional active pharmaceutical ingredient (API). In another embodiment, the at least one additional API is selected from the group consisting of: a non-steroidal anti-inflammatory drug; an opioid; a steroid; a tricyclic antidepressant; a gamma-Aminobutyric acid agonist; a local anaesthetic, such as lidocaine; a N-methyl-D-aspartate receptor antagonist, such as ketamine; an anti-oxidant; an anticonvulsant such as phenytoin; a TRPV1 receptor agonist; a TRPV1 receptor antagonist; an alpha-1 antagonist; a calcium channel blocker such as diltiazem or gabapentin; an alpha-2 agonist such as clonidine; an anti-psychotic, such as phenothiazine or chlorpromazine; and a counter irritant such as menthol, camphor, histamine or methyl nicotinate.

In another embodiment, the at least one additional API is selected from (i) the TRPV1 receptor agonist, (ii) the local anaesthetic, or (iii) both (i) and (ii). In another embodiment, the TRPV1 receptor agonist is capsaicin. In another embodiment, the counter irritant is menthol or camphor.

In another embodiment, the magnesium salt is magnesium chloride.

In another aspect, there is provided a transdermal ethosome composition comprising: an alcohol; a phospholipid; water; and a TRPV1 receptor agonist.

In one embodiment, the alcohol is present in an amount of between about 20-50% by weight of the composition, the phospholipid is present in an amount of between about 1-3% by weight of the composition, and the water is present in an amount of between about 20-70% by weight of the composition.

In another embodiment, the composition further comprises a glycol present in an amount of between about 5-20% by weight of the composition.

In another embodiment, the TRPV1 receptor agonist is capsaicin.

In another embodiment, the phospholipid comprises lecithin, a phospholipid derived from lecithin, or phosphatidyl choline.

In another embodiment, the alcohol is ethanol, isopropanol, or a combination thereof.

In another embodiment, the TRPV1 receptor agonist is present in an amount of at least about 0.15% by weight of the composition. In another embodiment, the TRPV1 receptor agonist is present in an amount of at least about 0.25% by weight of the composition.

In another embodiment, the composition further comprises at least one additional active pharmaceutical ingredient (API). In another embodiment, the at least one additional API is selected from the group consisting of: a non-steroidal anti-inflammatory drug; an opioid; a steroid; a tricyclic antidepressant; a gamma-Aminobutyric acid agonist; a local anaesthetic, such as lidocaine; a N-methyl-D-aspartate receptor antagonist, such as ketamine; an anti oxidant; an anticonvulsant, such as phenytoin; a TRPV1 receptor antagonist; a second TRPV1 receptor agonist; an alpha-1 antagonist; a calcium channel blocker, such as diltiazem or gabapentin; an alpha-2 agonist, such as clonidine; an antipsychotic, such as phenothiazine or chlorpromazine; and a counter irritant such as menthol, camphor, histamine or methyl nicotinate. In another embodiment, the counter irritant is menthol and/or camphor. In another embodiment, the menthol and camphor are each present in the composition in an amount of from about 0.5% to about 2.0% by weight of the composition, preferably about 2.0% by weight of the composition.

In another embodiment, the composition further comprises at least one salt selected from the group consisting of magnesium, calcium, and sodium salts. In another embodiment, the salt is present in an amount of between about 5.0-15.0% by weight of the composition. In another embodiment, the at least one salt is magnesium chloride.

In another aspect there is provided a method for transdermal delivery of magnesium, the method comprising topically applying the transdermal ethosome composition comprising a magnesium salt to a patient in need thereof. In another aspect there is provided a use of these transdermal ethosome composition for increasing subdermal concentration of magnesium.

In another aspect there is provided a use of the transdermal ethosome composition comprising a magnesium salt for the treatment of muscular pain. In one embodiment, the muscular pain is caused by one or more of muscle rigidity, Parkinson's disease, carpal tunnel syndrome, repetitive physical activity, a connective tissue disorder, a muscle and/or tendon disorder, myofascial pain syndrome, overexertion, muscle knots, fibromyalgia, post-exercise muscle soreness, sprain, muscle strain, tendonitis, and a musculoskeletal disorder. In another embodiment, the muscular pain is in one or more of the neck, back, shoulder, arm, hand, wrist, ankle, thigh, knee, calf, foot, elbow or hip.

In another aspect there is provided a use of the transdermal ethosome composition comprising a TRPV1 receptor agonist for the treatment of nociceptive pain or neuropathic pain. In one embodiment, the nociceptive pain or neuropathic pain is arthritis pain or fibromyalgia. In another embodiment, the nociceptive pain or neuropathic pain is in one or more of the neck, back, shoulder, arm, hand, wrist, ankle, thigh, knee, calf, foot, elbow or hip.

DETAILED DESCRIPTION OF THE INVENTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "suitable" as used herein means that the selection of the particular compound, component or conditions would depend on the specific formulation or manipulation to be performed, and the identity of the components to be formulated, and the selection of the compound, component or conditions would be well within the skill of a person trained in the art. All process/method steps described herein are to be conducted under conditions suitable to provide the product described. A person skilled in the art would understand that all formulation conditions, including, for example, selection of components, time, temperature, pressure, and component ratios can be varied to optimize the yield and properties of the described ethosome composition, and it is within their skill to do so.

The terms "drug" and "active pharmaceutical ingredient" (API) are used interchangeably and refer to a substance, such as a chemical compound, ion or complex, that has a beneficial physiological effect on the body, such as a therapeutic effect in treatment of a disease or disorder, when administered in an effective amount/dosage. Further, when these terms are used, or when a particular active agent is specifically identified by name or category, it is understood that such recitation is intended to include the active agent per se, as well as pharmaceutically acceptable and pharmacologically active derivatives thereof, or compounds significantly related thereto, including without limitation, pharmaceutically acceptable salts, prodrugs, active metabolites, isomers, fragments, analogs, solvates, solutions, solvate hydrates, radioisotopes, etc.

The phrases "effective amount" and "effective dosage" are used interchangeably and refer to that amount of a substance that produces some desired local or systemic effect at a reasonable benefit/risk ratio applicable to any treatment. The effective amount of such substance will vary depending upon the subject and disease condition being treated, the weight and age of the subject, the severity of the disease condition, the manner of administration and the like, which can readily be determined by one of ordinary skill in the art.

The term "ethosome" as used herein refers to a vesicle used to encapsulate at least one API for transdermal delivery and is a term of art that would be understood by a skilled person to include vesicles comprising a C2-C4 alcohol (e.g. ethanol), water, and phospholipid. Although the term "ethosome" is used herein, it would be understood to the skilled person that the alcohol used to make the ethosome could be any pharmaceutically acceptable C2-C4 alcohol. The ethosome is made by a combination of components in a method that encapsulates the API(s). The API can be added to the ethosome at any stage of preparation, although it is preferably added during formulation of the ethosome. Alternatively, the API can also be mixed with the ethosome after formulation, and the API will partition into the vesicles.

As used herein, the term "alcohol" refers to any pharmaceutically acceptable C2-C4 alcohol having one or more hydroxyl group. The alcohol used in the preparation of ethosomes can include, for example, one or more of ethanol, n-propanol, isopropanol, n-butanol, iso-butanol, sec-butanol and tert-butanol. The alcohol used to form the ethosome as described is preferably ethanol or isopropanol, and most preferably ethanol.

The term "pharmaceutically acceptable salt" is an art-recognized term and refers to the relatively non-toxic, inorganic and organic acid addition salts of compounds, including, for example, those contained in compositions described herein.

As used herein, the term "patient" refers to an animal, preferably a mammal, most preferably a human, and includes males, females and children.

The term "nociceptor" as used herein refers to a sensory neuron or nerve cell that responds to stimuli by sending nerve signals to the spinal cord and brain, usually causing the perception of pain. The term "nociceptor" and "pain receptor" are used interchangeably to refer to peripheral neurons that can detect mechanical, thermal or chemical changes above a set threshold. Nociceptors can be found in any area of the body that can sense pain. As used herein, the term "cutaneous nociceptors" is a nociceptor primarily found in tissues such as skin, cornea and mucosa. Some embodiments of the present compositions primarily target cutaneous nociceptors. The term "nociceptive pain" as used herein refers to pain resulting from the stimulation of one or more nociceptors.

As used herein, the term "vehicle" and "pharmaceutically acceptable vehicle" refers to the formulation of the composition and any optionally additional pharmaceutically acceptable excipients in which the presently described ethosomes can be formulated for transdermal delivery of the ethosome. The presently described compositions can be applied for transdermal delivery on their own, or can be combined with one or more pharmaceutically acceptable excipients. As would be understood to the skilled person, the ethosomes should be formulated in a way that renders them generally shelf stable over a reasonable period of time. Suitable pharmaceutically acceptable formulations include but are not limited to lotions, creams, gels, sprays, roll-ons, drops, ointments, liniments, pastes, balms, and solid formulations such as patches and adhesive solid gels.

The presently described composition is for the transdermal delivery of active pharmaceutical ingredients (APIs) to treat pain. Specifically, ethosome compositions are described for transdermal delivery of APIs to treat pain. Described are individual APIs that can be formulated in an ethosome for the transdermal treatment of pain, as well as a combination of APIs that can be formulated together in the same ethosome formulation, or used in different compositions simultaneously or sequentially, to treat pain. It is envisioned that the presently claimed compositions could avoid many of the side effects of muscle relaxants formulated for oral ingestion by delivering APIs directly to the site of the pain, rather than distributing them systemically (which, depending on the API, can lead to drowsiness, confusion and lethargy). In this way, systemic exposure of the patient to the API can be reduced. The presently described compositions treat the actual cause of the pain, specifically muscle tightness and excitation of nociceptors.

Some non-limiting examples of conditions which the presently described compositions can be used to treat include nocturnal night leg cramping, muscle cramping, muscle spasm, various types of muscle pain including neck and shoulder pain, rigidity such as that occurring in Parkinsonism, carpal tunnel syndrome, various pain-causing neuropathies, repetitive muscle injury such as that experienced by trades people or manual labourers who do manual work, muscle pain caused by exercising and/or playing sports, muscle pain resulting from physical activity (for example, shovelling snow), and facial muscle pain. Other non-limiting examples of conditions that can be treated with the presently described composition are musculoskeletal disorders, connective tissue disorders, neck and back pain, muscle and tendon disorders, foot and ankle disorders and/or pain, muscle pain from over-exertion (delayed-onset muscle soreness), myofascial pain syndrome, trigger points, muscle knots and fibromyalgia. The presently described compositions can also be useful in the treatment of minor injuries such as sprains, tendonitis, and post-exercise muscle soreness.

As described, magnesium cation ($Mg^{2+}$) delivered locally to muscles can assist in relaxation of muscle. Accordingly, an ethosome composition comprising a magnesium salt is provided for the treatment of pain having a muscular origin. Ethosome compositions for the treatment of muscular pain comprise a pharmaceutically acceptable form of magnesium ($Mg^{2+}$) cation in the form of a magnesium salt. The pharmaceutically acceptable salt of magnesium should be soluble in water so that the salt is in a dissolved form in the ethosome. In one embodiment, it is preferable that the magnesium salt have a low molecular weight to maximize the concentration of magnesium in aqueous solution. In other embodiments, the magnesium cation may be in the form of a salt whose anion is also pharmaceutically active. Exemplary pharmaceutically acceptable salts of magnesium include chloride and sulfate salts, in particular chloride. Non-limiting additional examples of other pharmaceutically acceptable magnesium salts are magnesium bromide, gluconate, malate, and citrate.

The magnesium salt is preferably added during manufacture of the ethosome in the form of a salt solution. The amount of magnesium salt in the salt solution can range from as little as 1.0% to as much as to 34.0% by weight of the salt solution, with the upper limit bounded by the solubility of the magnesium salt in water. The final amount of magnesium salt in the ethosome composition is calculated based on the initial amount of salt in the magnesium salt solution and the proportion of salt solution in the final ethosome composition. In some embodiments, it may be preferable to use pre-prepared salt solutions with a maximal concentration of magnesium salt in water. Solutions of ultra high concentration of magnesium chloride salt in water are sometimes referred to as "magnesium oil," and are near saturated, saturated or supersaturated solutions. Such magnesium salt solutions will maximize the amount of magnesium salt in the ethosome, which can be up to about 13.0-15.0% magnesium salt by weight. In one embodiment, the amount of magnesium salt in the ethosome composition is up to about 15.0% by weight of the total ethosome composition. In some embodiments, the amount of magnesium salt in the ethosome composition is between about 1.0% and 15.0% by weight, in other embodiments the amount of magnesium salt in the ethosome composition is between about 5.0-15.0% by weight, and in yet other embodiments the amount of magnesium salt in the ethosome composition is between about 10.0-15.0% by weight of the total composition.

Ethosome compositions for the treatment of pain involving pain sensing neurons preferably comprise a TRPV1 receptor agonist, such as, for example capsaicin, or a TRPV1 receptor antagonist. Capsaicin, one TRPV1 agonist, has been used to treat pain caused by stimulation of cutaneous nociceptors. One problem with using a high strength of capsaicin is the burning sensation it causes to the skin. In high concentrations, patients have a difficult time tolerating the burning of capsaicin. However, if the capsaicin is coated in a vesicle such as an ethosome, then the ethosome can pass the nerve terminals located in the skin with minimal burning sensation. Concentrations of capsaicin in the ethosome composition of at least 0.1% can be used, preferably at least 0.15% and more preferably at least 0.25% by weight of the composition. However, it has also been found that the addition of menthol and/or camphor to the ethosome composition can increase the patient tolerance for capsaicin in the composition. Formulation of capsaicin in an ethosome has been found to significantly reduce the topical burning sensation experienced by the patient. Accordingly, increasing the amount of capsaicin in the composition to greater than 0.25%, or greater than 0.5%, or even up to and greater than 1.0% by weight of the composition is possible.

In addition, the topical ethosome compositions described herein can be used to treat pain having a neurological derivation, since $Mg^{2+}$ has also been shown to have positive effects on the treatment of neurological pain, such as for example, pain resulting from the stimulation of glutamate receptors. Magnesium salt and a TRPV1 receptor agonist or antagonist can be combined together in the same ethosome composition, or can be used simultaneously or sequentially in different ethosome compositions, for the treatment of complex pain having both muscular and neurological derivations.

Ethosome compositions as presently described comprise at least one alcohol selected from ethanol and isopropanol, together with water and phospholipid. The alcohol serves as a permeation enhancer in ethosomes and is believed to disturb the skin lipid bilayer in the stratum corneum, increasing cell membrane lipid fluidity and decreasing the density of the lipid multilayer of cell membrane. The present ethosome compositions comprise ethanol or isopropanol or a combination thereof. The ethosome can also include other C3-C4 alcohols which include n-propanol, n-butanol, isobutanol, sec-butanol and tert-butanol. The preferable amount by weight of alcohol in the ethosome is 20-50%, with 30-45% being preferable, and about 40-45% being most preferable. Previous studies that used different amounts of alcohol suggest that increasing the alcoholic content of the ethosome corresponds to a decrease in the vesicle size and better penetration (Paolino, D. et al. *Journal of Controlled Release*, Vol. 106, pp. 99-110, 2005).

The variation in the percentage of alcohol depends on the nature of the drug or API for entrapment. The more lipophilic the drug is, the less alcohol is required. The more hydrophilic the drug is the more alcohol is required to aid in its penetration of the skin. In an initial trial using only magnesium salt as the API (which is a hydrophilic polar molecule), alcohol percentages of as high as 45% wt were used. In other trials using capsaicin (a highly lipophilic molecule) as the API, the percentage of alcohol in the ethosome could be decreased without detrimental effect on the permeation of capsaicin through the skin. In combination with alcohol, water is also present in the ethosome in an amount of between 20-70% by weight of the ethosome composition.

The role of the phospholipid in the ethosome composition is in the formation of the ethosome vesicle. The phospholipid also contributes to the penetration efficiency of the ethosome through the skin. Various phospholipids can be used in the presently described compositions. Such phospholipids can be extracted from lecithin from eggs, soybean, rapeseed (canola) or sunflower, or can be obtained synthetically. Some non-limiting examples of phospholipids are phosphatidylcholine (PC), hydrogenated PC, phosphatidic acid (PA), phosphatidylserine (PS), phosphatidylethanolamine (PE), phosphatidylglycerol (PPG), phosphatidylinositol (PI), hydrogenated PC, glycerophosphocholine, and sphingomyelin. These can be used individually, or as a combination of one or more phospholipids. Lecithin and phospholipids derived therefrom are preferable because lecithin is already approved for use as a pharmaceutical excipient, is derived from food sources, is available from organic sources, is not expensive and is readily available. Lecithin is a mixture of phospholipids that consists mainly of phosphatidyl choline and small percentage of other phospholipids. One preferable phospholipid is soybean-derived pure phosphatidyl choline, commercially available as Phospholipon™. Pure phosphatidyl choline derived from lecithin has been shown to have a good combination of vesicle stability, entrapment efficiency, and patient acceptability.

In previous studies, it was found that the higher the concentration of the phospholipid in the vesicle, the higher the entrapment efficiency and the higher rigidity of the vesicle. Increasing the amount of phospholipid in the ethosome has also been found to result in an increase in size of the ethosome (Touitou et al. *Journal of Controlled Release*, Vol. 65 (2000) 403-418). The amount of phospholipid by weight of the concentration should be in the range of about 0.5%-10.0%, with a preferable amount about 1%-3%, most preferably about 2%. Previously reported methods for manufacture of ethosomes reported use of about 2% by weight phospholipid, however greater than 3% by weight phospholipid has been used in ethosome compositions to good effect.

Cholesterol can also be optionally added to the composition to increase stability of the ethosomes. Cholesterol can also increase the entrapment efficiency, however it can also decrease the flexibility of the ethosomes. A range of cholesterol by weight in an amount of between 0.1%-2.0% can optionally be used. In the formulation of highly hydrophilic chemical species such as magnesium salt, cholesterol can be used to increase the entrapment efficiency of the API as much as possible. In cases where cholesterol is used, an amount of cholesterol of preferably about 0.2-1.0% by weight, and most preferably 0.2% by weight can be added. Cholesterol can be obtained as a natural product from sheep wool, other animal sources and synthetic sources.

In the ethosome composition, glycol provides a negative charge to the vesicle preventing its aggregation, works as a penetration enhancer and facilitates entrapment of the API in the ethosome. Glycols can be single monomers comprising at least two hydroxyl groups, or can be dimers or polymers comprising more than two hydroxyl groups. Various glycols can be used, including polyethylene glycol, propylene glycol, ethoxy diglycol, diethyleneglycol monoethyl ether, or a combination thereof, with polyethylene glycol, ethoxy diglycol or a combination thereof being preferable.

Manconi et al. have reported a stabilizing effect of propylene glycol (PG) in formulations against aggregation of vesicles (Colloids and Surfaces *A: Physicochem. Eng. Aspects* Vol. 342 pp. 53-58, 2009). Zhou et al. have also reported that a combination of an alcohol phase comprised of ethanol and propylene glycol improves the stability of the resulting ethosomes (Zhang, J-P. et al., *Archives of Pharmacal Research*, vol. 35(1), pp. 109-117, 2012). When making an ethosome composition with a hydrophilic drug like magnesium salt, glycol is required to provide penetration enhancement. Lipophilic drugs will require less glycol since hydrophilic drugs need less or no penetration enhancement. It has also been found that propylene glycol and ethoxy diglycol can be used in combination with both hydrophilic cations such as magnesium as well as with lipophilic APIs such as capsaicin. It has also been found that ethosome compositions comprising lipophilic APIs such as capsaicin often do not require a penetration enhancer and can be formulated without glycol. Where glycol is present in the ethosome composition, in one embodiment the glycol is present in an amount of from about 5-20% by weight in the composition. In other embodiments, the glycol is present in an amount of from about 8-15% by weight in the composition, and in other embodiments the glycol is present in an amount of from about 9-10% by weight in the composition.

Other glycols such as 2-(2-Ethoxyethoxy)ethanol (Transcutol™) can also be optionally added to the ethosome composition. Non-ionic surfactants can also be added, such as PEG-alkyl ethers. Cationic lipids such as cocoamide, POE alkyl amines, dodecylamine, and centrimide can also be included.

The ethosome composition can also comprise additional components or APIs that have been found to be effective in the treatment of muscular pain. Two preferable examples are camphor and menthol, both of which are known to produce a feeling of cooling and act as slight local anaesthetics and/or counter irritants. Menthol has been used widely in topical formulations to stimulate the transient receptor potential cation channel subfamily M member 8 (TRPM8) receptor, which causes a cool sensation and numbing of the pain. Menthol is also known to work as a sodium channel blocker on alpha nerve fibres, as well as on opioid receptors or kappa receptors, and has demonstrated vasomodulating effects on blood vessels, which increases blood flow to the area of application. TRPM8 allows the entry of $Na^+$ and $Ca^{2+}$ ions to the cell that leads to depolarization and the generation of an action potential, leading to the sensation of cold. Accordingly formulation of menthol with pharmaceutically acceptable salts of cations such as $Na^+$, $Mg^{2+}$ and Ca$^{2+}$ may lead to synergistic activation of TRPM8. Pharmaceutically acceptable salts of magnesium are noted above, and corresponding pharmaceutically acceptable salts of sodium and calcium can likewise be used (e.g. chloride, sulfate, etc.).

Some other non-limiting examples of additional APIs that can be used in combination with magnesium salt and/or a TRPV1 receptor agonist or antagonist in the present composition are: non-steroidal anti-inflammatory drugs (NSAIDs) such as diclofenac, diethylamine and diclofenac sodium; opioids such as ketamine, meperidine and morphine; steroids such as dexamethasone; tricyclic antidepressants such as amitriptyline; gamma-Aminobutyric acid (GABA) agonists such as gabapentin, neurontin and baclofen; local anaesthetics such as lidocaine; N-methyl-D-aspartate (NMDA) receptor antagonists, such as ketamine; anti oxidants; anticonvulsants such as phenytoin; alpha-1 antagonists; calcium channel blocker such as diltiazem and gabapentin; alpha-2 agonists such as clonidine, phenothiazine and chlorpromazine; and counter irritants such as histamine, methyl nicotinate, menthol and camphor. Menthol and camphor can also be considered to have anaesthetic properties and function as a local anaesthetic.

The present compositions can also comprise herbal extracts. One example of an herbal extract that can be used in the present compositions is *rosmarinius officinalis* (rosemary) extract, which also contains camphor.

The present ethosome composition can be formulated in various pharmaceutically acceptable vehicles suitable for transdermal application and administration. Non-limiting examples of pharmaceutically acceptable vehicles for topical administration of the present compositions include single and multiple-component vehicles such as lotions, creams, gels, roll-ons, sprays, drops, ointments, liniments, pastes, balms, patches and adhesive solid gels. The transdermal ethosome compositions should be applied topically by covering the affected area and those areas immediately surrounding same. In general, it is contemplated that an effective amount or dosage of the ethosome compositions described herein would be a treatment of about one to four times daily for at least about 5 days. The compositions can also be used for an extended period of time, as required. It is also contemplated that the compositions can be used only once, every other day, or on an as necessary basis. It will be apparent to those of skill in the art that the effective amount may be lowered or increased depending on the response of the treated subject. For compositions comprising capsaicin, increasing the amount of capsaicin in the composition can decrease the number of times a day dosing is required to achieve the desired effect. The effective dosage mentioned hereinabove is therefore a guideline only and is not intended to limit the scope or use of the invention in any way.

General Method

The ethosome compositions can be prepared based on literature methods (Touitou et al. *Journal of Controlled Release* 65 (2000) 403-418; Akiladevi, D. and Basak, A. *International Journal of Current Pharmaceutical Research* Vol. 2(4), pp. 1-4, 2010). The following exemplary method is described for obtaining the ethosome composition A2. For compositions comprising a lipophilic API, such as diclofenac diethylamine or capsaicin, the lipophilic API is added to the alcoholic component prior to mixing the alcoholic component with the aqueous component, with diclofenac in the method being exemplary of a lipophilic API. Menthol and camphor are also considered to be lipophilic. For compositions comprising a hydrophilic API, the hydrophilic API is added to the aqueous component with the phospholipid and water. The salt, for example magnesium chloride as described in the following example, is hydrophilic and preferably pre-dissolved in water to ensure complete dissolution. If no salt is to be included in the composition, the aqueous component will be prepared without salt, such as in the compositions shown in Table 2.

To prepare the aqueous component, the MgCl$_2$ sol (47.0 g, aqueous solution of comprising 30% by weight magnesium chloride) was added to a stainless steel container. Phosphatidyl choline (2.0 g) and cholesterol (0.2 g) were added to the stainless steel container and mixed at an agitator speed of 40 rpm with the MgCl$_2$ solution to obtain a homogenous suspension. For the alcoholic component, in a main tank, the diclofenac diethylamine (1.16 g) and ethanol (41.64 g) were mixed at an agitator speed of 40 rpm to obtain a clear solution. The propylene glycol (7.8 g) was then added to the main tank. The contents of the stainless steel container was then added to the main tank and mixed at an agitator speed of 40 rpm to obtain a homogenous solution. Stabilenhance® (0.2 g, an antioxidant) was then added to the main tank and mixed to obtain a homogenous solution, then homogenized at a homogeniser speed of 3000 rpm to obtain a hazy solution.

To prepare compositions comprising additional APIs, the additional API can be added either to the water or the alcohol, depending on its lipophilicity. If the API is lipophilic then it is dissolved in the alcohol prior to mixing the alcoholic mixture with the aqueous mixture. When the ethosome composition comprises capsaicin, capsaicin is dissolved in the alcohol, which is then mixed with the aqueous components. If the API is hydrophilic, then it is added to the aqueous mixture prior to mixing the aqueous mixture with the alcoholic mixture.

To gain a better understanding of the invention described herein, the following examples are set forth. It should be understood that these examples are for illustrative purposes only. Therefore, they should not limit the scope of this invention in any way.

EXAMPLES

Example 1: Ethosome Composition with Magnesium Salt

In the compositions described, magnesium chloride is used. However, any pharmaceutically acceptable magnesium salt can be used, as previously described. The concentration of aqueous MgCl$_2$ solution used in the compositions listed in Table 1 is 30% by weight. This high concentration solution is available as a super saturated aqueous solution, also sometimes referred to as magnesium oil. In composition A1, for example, beginning with an aqueous solution of about 30% MgCl$_2$ by weight, the amount of MgCl$_2$ in the final concentration is about 14.34% by weight of the final ethosome composition. Natrox® is a commercially available antioxidant/preservative. Sensehot® is vanillyl butyl ether.

The compositions were prepared according to the general method set out above. Various compositions with magnesium salt were prepared. Exemplary compositions are shown in Table 1.

TABLE 1

| Component | Compositions (wt %) | | | | | | | | | |
|---|---|---|---|---|---|---|---|---|---|---|
| | A1 | A2 | A3 | A4 | A5 | A6 | A7 | A8 | A9 | A10 |
| Water | 0.00 | 0.00 | 0.00 | 0.00 | 0.00 | 16.00 | 16.00 | 0.00 | 0.00 | 0.00 |
| $MgCl_2$ Sol (30%) | 47.8 | 47.00 | 41.00 | 41.00 | 41.00 | 20.00 | 20.00 | 41.00 | 41.00 | 41.00 |
| Cholesterol | 0.2 | 0.20 | 0.10 | 0.10 | 0.10 | 0.10 | 0.10 | 0.20 | 0.10 | 0.00 |
| Phosphatidyl Chloline | 2.00 | 2.00 | 3.00 | 2.00 | 2.00 | 2.00 | 2.00 | 2.00 | 2.00 | 2.00 |
| Propylene Glycol | 10.0 | 7.80 | 7.80 | 9.40 | 9.40 | 9.40 | 14.40 | 9.20 | 9.20 | 9.40 |
| Menthol | 0.00 | 0.00 | 0.00 | 2.00 | 2.00 | 12.00 | 0.00 | 2.00 | 2.00 | 2.00 |
| Camphor | 0.00 | 0.00 | 0.00 | 2.00 | 2.00 | 0.00 | 3.00 | 2.00 | 2.00 | 2.00 |
| Ethanol | 40.0 | 41.64 | 40.74 | 0.00 | 0.00 | 40.00 | 44.00 | 40.10 | 40.00 | 40.00 |
| Sensehot ® | 0.00 | 0.00 | 0.00 | 0.00 | 0.00 | 0.00 | 0.00 | 0.00 | 0.20 | 0.00 |
| Ethoxy-diglycol | 0.00 | 0.00 | 6.00 | 3.00 | 3.00 | 0.00 | 0.00 | 3.00 | 3.00 | 3.00 |
| Diclofenac | 0.00 | 1.16 | 1.16 | 0.00 | 0.00 | 0.00 | 0.00 | 0.00 | 0.00 | 0.00 |
| Isopropyl Alcohol | 0.00 | 0.00 | 0.00 | 40.00 | 40.00 | 0.00 | 0.00 | 0.00 | 0.00 | 0.00 |
| Natrox ® | 0.00 | 0.00 | 0.00 | 0.50 | 0.50 | 0.50 | 0.50 | 0.00 | 0.00 | 0.00 |
| Stabilenhance ® | 0.00 | 0.20 | 0.20 | 0.00 | 0.00 | 0.00 | 0.00 | 0.50 | 0.50 | 0.50 |

Testing of Ethosome Composition with Magnesium Salt

The present compositions have been used with patients, with their full and informed consent. The ethosome compositions were formulated for spray application.

It has been found that the ethosome composition with magnesium salt is highly effective in releasing muscle spasms especially with superficial muscles, for example neck, shoulder and calf muscles. Preferably, the compositions should be applied regularly for five to ten days to obtain the full effect. In some patients, significant relief is not experienced until a few days after beginning treatment.

Composition A1 was tested on patient D. J., an 80 year-old male. Mr. D. J. complained of muscles cramps in his feet and calf muscles waking him up from sleep. Patient was able to sleep through the night after using the ethosome composition A1.

Mrs. M. L. is a 60 year old woman. She suffered from constant neck and shoulder pain and was diagnosed with arthritis in her neck vertebrae. She often complained about a stiff neck and she was getting massage and acupuncture treatment for same. Mrs. M. L. tried the ethosome composition A3 and started noticing a relief. Her acupuncturist even noticed that her neck and shoulder muscles were not as stiff as they had been previously. She has been using the product for the past 6 months with no side effects.

Mr. L. S. is an 82 year old man. He complained from nocturnal cramps in his calf muscles that would wake him up from sleep at night. He tried applying ethosome composition A5 with magnesium chloride in combination with menthol and camphor before going to sleep. He has had complete relief from his muscle cramps since beginning treatment.

Mr. R. C. is an over 50 year old handyman. Due to the physical requirement of his work, Mr. R. C. complains of constant muscle spasms. Mr. R. C. has been using the ethosome compositions A5 and A8 with magnesium chloride in combination with menthol and camphor on an as needed basis whenever he has a tough day and has experienced relief from his muscle spasms.

Mr. H. R. is a 47 year old computer programmer. Mr. H. R. suffers from shoulder and neck pain which developed into a constant headache. His pain was diagnosed to be due to muscle tightness from sitting for long hours working on the computer. Mr. H. R. has enjoyed a big improvement since he started using the ethosome composition A9 and A10 with magnesium in combination with menthol and camphor. Mr. H. R. uses the product regularly now to prevent this pain and headache from recurring.

Example 2: Ethosome Composition with a TRPV1 Agonist

Ethosome compositions comprising capsaicin have been made and tested with patients. Since the capsaicin in the present ethosome compositions can bypass the skin with minimal irritation compared to what may be experienced by application of alcoholic capsaicin solution (See Example 4), it would be understood that higher amounts of capsaicin would be desirable in ethosome formulations providing that the same does not cause intolerable skin irritation in patients. Amounts of capsaicin in the composition of between 0.15% to 0.5% have been tried with patients. It is expected that amounts of capsaicin in an ethosome composition up to and greater than 1.0% in combination with camphor and/or menthol can also be formulated and well-tolerated by patients.

When formulated with capsaicin, camphor has been found to increase a patient's tolerance for capsaicin. The addition of camphor to an ethosome composition comprising capsaicin has demonstrated improved patient tolerance compared to capsaicin alone. The addition of menthol has also demonstrated improved tolerance and patient acceptance for the ethosome composition comprising capsaicin compared to capsaicin alone.

Various compositions were prepared comprising capsaicin, as shown in Table 2. Menthol can optionally be added to overcome the burning sensation caused by the capsaicin. Menthol in an amount of 10% can cause a burning sensation on its own, and an FDA Safety Announcement on Sep. 13, 2012 has reported that skin can burn with menthol concentrations above 3% (http://www.fda.gov/Drugs/DrugSafety/ucm318858.htm). Thus, in one embodiment, the concentration of menthol in the ethosome compositions is less than about 3% by weight. In another embodiment, the concentration of menthol in the ethosome compositions is about 2% by weight.

Capsaicin is a lipophilic drug, and therefore has a sufficiently high entrapment efficiency in the ethosome composition so as not to require the use of cholesterol. However, it is conceivable that cholesterol may be desirable in some compositions comprising capsaicin. In a combination composition comprising magnesium salt and capsaicin, such as those shown in Table 3, it is preferable to use some cholesterol to improve the entrapment efficiency of the magnesium salt in the ethosome.

TABLE 2

| Component | Compositions (wt %) | | | | | | |
|---|---|---|---|---|---|---|---|
| | B1 | B2 | B3 | B4 | B5 | B6 | B7 |
| Water | 38.00 | 42.00 | 44.00 | 41.00 | 41.00 | 40.00 | 40.00 |
| Cholesterol | 0.00 | 0.20 | 0.20 | 0.20 | 0.10 | 0.10 | 0.10 |
| Phosphatidyl Chloline | 2.00 | 2.00 | 2.00 | 2.00 | 2.00 | 3.00 | 3.00 |
| Propylene Glycol | 9.25 | 9.05 | 9.40 | 9.40 | 9.40 | 9.40 | 9.80 |
| Ethoxydiglycol | 0.00 | 0.00 | 0.00 | 3.00 | 3.00 | 3.00 | 3.00 |
| Ethanol 99.5% | 46.00 | 42.00 | 39.65 | 39.65 | 39.75 | 39.75 | 39.75 |
| Capsaicin | 0.25 | 0.25 | 0.25 | 0.25 | 0.25 | 0.25 | 0.15 |
| Menthol | 2.00 | 2.00 | 2.00 | 2.00 | 2.00 | 2.00 | 2.00 |
| Camphor | 2.00 | 2.00 | 2.00 | 2.00 | 2.00 | 2.00 | 2.00 |
| Stabilenhance | 0.50 | 0.50 | 0.50 | 0.50 | 0.50 | 0.50 | 0.20 |

Experimentation was performed to determine the amount of phospholipid required to formulate the capsaicin ethosomes. A clear formula was obtained with 3% phospholipid. Either naturally sourced or synthetic capsaicin can be used, and exemplary compositions were made using both. The selection of natural vs. synthetic capsaicin may be made based on regulatory requirements. It was found that synthetic capsaicin required only about 2% phospholipid by weight in the composition compared to naturally sourced capsaicin which seemed to require more than 2% phospholipid.

Testing of Ethosome Composition with Magnesium Salt and TRPV1 Agonist

An ethosome composition having only capsaicin as an API does not require formulation with cholesterol as capsaicin is highly lipophilic, accordingly, there is no need to strengthen the vesicles with the cholesterol. The ethosome composition was provided as a roll on. All patients provided their full and informed consent.

Mr. Y. M. is a 55 year old male who has suffered from arthritis in the hand for a long time. His arthritis does not respond to traditional treatments. He tried an ethosome composition comprising 0.25% capsaicin and experienced a great relief. He mentioned that the burning sensation was tolerable and it went away after applying the product for a week to 10 days. He mentioned that he need to be extra cautious not to touch his eyes as this can result in burning sensation and tearing of his eyes. After beginning treatment, Mr. Y. M. has continued to regularly used the capsaicin ethosome composition twice daily for at least 4 months. Mr. Y. M. tested compositions B1, B2 and B5.

Mr. M. B. is in his mid-fifties and suffers from knee pain. He tried an ethosome composition comprising 0.25% capsaicin for 5 days with no results. He was counselled to continue using the product as the results sometimes take some time to show. Ten days later Mr. M. B. came back reporting a great relief of his pain. Mr. M. B has been using composition B6 since then with no complaints.

Example 3: Ethosome Composition with Magnesium Salt and a TRPV1 Agonist

In cases where patients experience their pain as a combination of muscle tightness or muscular in origin and neurological pain or nociceptor-related pain, a synergistic effect between $Mg^{2+}$ and capsaicin may be observed. Specifically, magnesium can act on the muscles to induce muscle relaxation at the same time that capsaicin will act on TRPV1 to reduce neurological pain. In addition, extracellular $Na^+$, $Mg^{2+}$, and $Ca^{2+}$ ions have also been shown to sensitize and activate the TRPV1 receptor (Ahern, G. P. et al. *The Journal of Neuroscience*, Vol. 25(21), pp. 5109-5116, 2005). However, in a topical formulation, it can be a challenge to encapsulate both $Mg^{2+}$, a highly hydrophilic chemical species, with capsaicin, a highly lipophilic chemical species. When the magnesium chloride is added to the ethosome composition, cholesterol is generally required to achieve sufficient entrapment efficiency.

A number of ethosome compositions comprising both magnesium salt and capsaicin were prepared, representative examples of which are shown in Table 3.

TABLE 3

| Component | Compositions (wt %) | | |
|---|---|---|---|
| | C1 | C2 | C3 |
| $MgCl_2$ Sol (30%) | 41.00 | 41.00 | 41.00 |
| Cholesterol | 0.10 | 0.10 | 0.10 |
| Phosphatidyl Chloline | 3.00 | 3.00 | 3.00 |
| Propylene Glycol | 9.40 | 9.80 | 9.40 |
| Ethoxydiglycol | 3.00 | 3.00 | 3.00 |
| Menthol | 2.00 | 2.00 | 2.00 |
| Capsaicin | 0.25 | 0.15 | 0.25 |
| Ethanol | 0.00 | 40.75 | 40.75 |
| Isopropyl Alcohol | 40.75 | 0.00 | 0.00 |
| Natrox | 0.50 | 0.0 | 0.00 |
| Stabilenhance | 0.00 | 0.20 | 0.50 |

Testing

The C1-C3 compositions were formulated as a roll-on. Composition C1 was tested on a patient, with full and informed consent. Composition C1 comprises capsaicin with magnesium chloride without camphor. After a few days the patient complained of burning. It was found that by adding 0.5% camphor the burning sensation became tolerable to the patient.

Mrs. U. S. is a 55 year old female who suffers from neuropathic pain in her calf muscle. She tried composition C1 including 0.5% camphor but could not tolerate the burning. The formulation was adjusted to increase the concentration of camphor to 2%. The patient was able to tolerate the burning sensation in the resulting composition and she enjoyed a great relief from her calf pain. Mrs. U. S. has been using the ethosome composition with magnesium chloride and capsaicin for the past 2 months.

Mrs. M. B. is in her late forties and working as a cleaning lady. Mrs. M. B. suffers from knee arthritis that prevents her from working. She was extremely pleased with the results that she obtained from ethosome composition C3. She even cried and hugged the pharmacist who had provided the composition to her when she was providing him with feedback. She said that the relief she experienced had never been attained before by any other treatment.

Example 4: Comparison of Capsaicin in Ethanol Vs. Ethosomes

A comparison was done between the burning sensation caused by use of 0.25% capsaicin in ethyl alcohol (alcoholic solution) and the same strength of capsaicin in ethosomes. The preparation with the alcohol was found to induce far more burning sensation than the compositions comprising capsaicin with ethosomes. The alcoholic composition was tested on three patients, with full and informed consent, though all complained of painful burning.

The same handyman mentioned above, Mr. R. C., has severe knee arthritis. An alcoholic solution of 0.25% capsaicin spray was tested and compared with an ethosomal composition comprising only capsaicin as the API, an ethosomal composition comprising capsaicin and menthol, and an ethosomal composition comprising magnesium chloride, camphor, capsaicin and menthol, all formulated for spray application. The pain relief was noticeable with all the compositions tested, however the patient complained that the hydro alcoholic solution with capsaicin (non-ethosome composition) felt severely hot. All of the other ethosome-based compositions were well tolerated and provided noticeable pain relief.

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. The scope of the claims should not be limited to the preferred embodiments set for the description, but should be given the broadest interpretation consistent with the description as a whole.

The embodiments of the invention in which an exclusive property or privilege is claimed are defined as follows:

1. A transdermal ethosome composition comprising:
   an alcohol;
   a phospholipid;
   a glycol;
   water; and
   a magnesium salt.
2. The composition of claim 1, wherein the alcohol is present in an amount of between about 20-50% by weight of the composition, the phospholipid is present in an amount of between about 0.5-10% by weight of the composition, the glycol is present in an amount of between about 5-20% by weight of the composition, and the water is present in an amount of between about 20-70% by weight of the composition.
3. The composition of claim 1, wherein the magnesium salt is present in the ethosome composition in an amount of between about 5.0-15.0% by weight of the composition.
4. The composition of claim 1, wherein the phospholipid comprises lecithin, a phospholipid derived from lecithin, or phosphatidyl choline.
5. The composition of claim 1, wherein the alcohol is ethanol, isopropanol, or a combination thereof.
6. The composition of claim 1, further comprising at least one additional active pharmaceutical ingredient (API).
7. The composition of claim 6, wherein the at least one additional API is selected from the group consisting of: a non-steroidal anti-inflammatory drug; an opioid; a steroid; a tricyclic antidepressant; a gamma-Aminobutyric acid agonist; a local anaesthetic; a N-methyl-D-aspartate receptor antagonist; an anti-oxidant; a TRPV1 receptor agonist; a TRPV1 receptor antagonist; an alpha-1 antagonist; a calcium channel blocker; an alpha-2 agonist; an antipsychotic; a counter irritant; and mixtures thereof.
8. The composition of claim 7, wherein the at least one additional API is selected from (i) the TRPV1 receptor agonist, (ii) the counter irritant, or (iii) both (i) and (ii).
9. The composition of claim 7, wherein the TRPV1 receptor agonist is capsaicin.
10. The composition of claim 7, wherein the counter irritant is selected from the group consisting of menthol, camphor, histamine, methyl nicotinate, and mixtures thereof.
11. The composition of claim 1, wherein the magnesium salt is magnesium chloride.
12. A transdermal ethosome composition comprising:
    an alcohol;
    a phospholipid;
    water; and
    a first TRPV1 receptor agonist,
    wherein the first TRPV1 receptor agonist is capsaicin, and
        wherein the capsaicin is present in the amount of at least 0.15% by weight of the composition.
13. The composition of claim 12, wherein the alcohol is present in an amount of between about 20-50% by weight of the composition, the phospholipid is present in an amount of between about 0.5-10% by weight of the composition, and the water is present in an amount of between about 20-70% by weight of the composition.
14. The composition of claim 1, further comprising a glycol present in an amount of between about 5-20% by weight of the composition.
15. The composition of claim 12, wherein the phospholipid comprises lecithin, a phospholipid derived from lecithin, or phosphatidyl choline.
16. The composition of claim 12, wherein the alcohol is ethanol, isopropanol, or a combination thereof.
17. The composition of claim 12, wherein the capsaicin is present in an amount of at least about 0.25% by weight of the composition.
18. The composition of claim 12, further comprising at least one additional active pharmaceutical ingredient (API).
19. The composition of claim 18, wherein the at least one additional API is selected from the group consisting of: a non-steroidal anti-inflammatory drug; an opioid; a steroid; a tricyclic antidepressant; a gamma-Aminobutyric acid agonist; a local anaesthetic; a N-methyl-D-aspartate receptor antagonist; an anti oxidant; an anticonvulsant; a TRPV1 receptor antagonist; a second TRPV1 receptor agonist; an alpha-1 antagonist; a calcium channel blocker; an alpha-2 agonist; an antipsychotic; and mixtures thereof.
20. The composition of claim 19, wherein the counter irritant is selected from the group consisting of menthol, camphor, histamine, methyl nicotinate, and mixtures thereof.
21. The composition of claim 20, wherein the menthol and camphor are each present in the composition in an amount of from about 0.5% to about 2.0% by weight of the composition.
22. The composition of claim 12, further comprising at least one salt selected from the group consisting of magnesium, calcium, and sodium salts.
23. The composition of claim 22, wherein the salt is present in an amount of between about 5.0-15.0% by weight of the composition.
24. The composition of claim 22, wherein the at least one salt is magnesium chloride.

* * * * *